United States Patent [19]

Peyton et al.

[11] Patent Number: 4,546,247

[45] Date of Patent: Oct. 8, 1985

[54] CHIPPED NECK INSPECTOR

[75] Inventors: John J. Peyton; Bryan K. Watt, both of Santa Barbara, Calif.

[73] Assignee: Industrial Automation Corp., Goleta, Calif.

[21] Appl. No.: 656,492

[22] Filed: Oct. 1, 1984

Related U.S. Application Data

[63] Continuation of Ser. No. 319,062, Nov. 6, 1984.

[51] Int. Cl.$^4$ .............................................. G01V 9/04
[52] U.S. Cl. .................................. 250/223 B; 356/240
[58] Field of Search ............... 250/209, 223 R, 223 B, 250/578; 356/240; 209/524, 526, 529

[56] References Cited

U.S. PATENT DOCUMENTS

| | | | |
|---|---|---|---|
| 3,349,906 | 10/1967 | Calhoun et al. | 250/223 B |
| 3,533,704 | 10/1970 | Krenmayr | 250/223 B |
| 3,791,741 | 2/1974 | Brenholdt | 250/223 B |
| 3,880,750 | 4/1975 | Butler et al. | 250/223 B |
| 3,980,890 | 9/1976 | Heckrodt et al. | 250/223 B |
| 4,026,414 | 5/1977 | Ellinger | 356/240 |
| 4,293,219 | 10/1981 | Ducloux | 356/240 |
| 4,391,373 | 7/1983 | Wiggins | 209/526 |

Primary Examiner—David C. Nelms
Attorney, Agent, or Firm—Blakely, Sokoloff, Taylor & Zafman

[57] ABSTRACT

A mechanism for automatically inspecting the condition of the lip of a container. A beam or pulse of energy is directed by a first energy guide to impact upon a portion of the lip of a container. The amount of energy, reflected off the lip and through a second energy guide, is measured by a sensor located at the end of the second guide. The sensor produces an output signal having a magnitude proportional to the amount of reflected energy received by the sensor. Appropriate electrical circuitry compares the magnitude of the sensor output to a preselected magnitude. If the sensor output is greater it generates a first signal indicating a first condition of that portion of the lip of the container and, if the sensor output is less it generates a second signal indicating a second condition of that portion of the lip. A plurality of such reflected beams and sensors and electrical circuits may be employed around the perimeter of the lip to determine the condition of substantially the entire lip.

12 Claims, 10 Drawing Figures

U.S. Patent  Oct. 8, 1985  Sheet 1 of 6  4,546,247
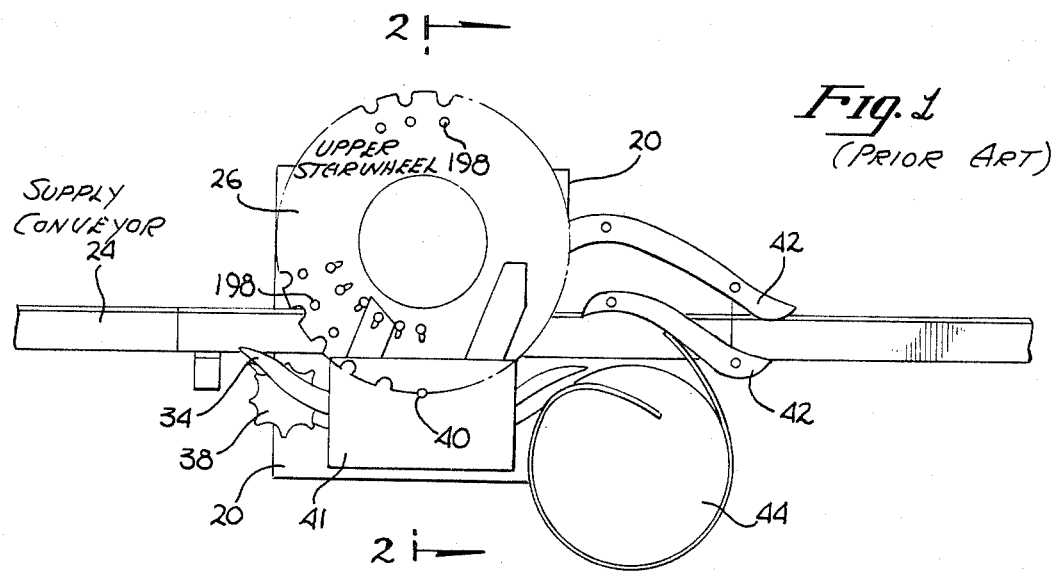
Fig. 1
(PRIOR ART)
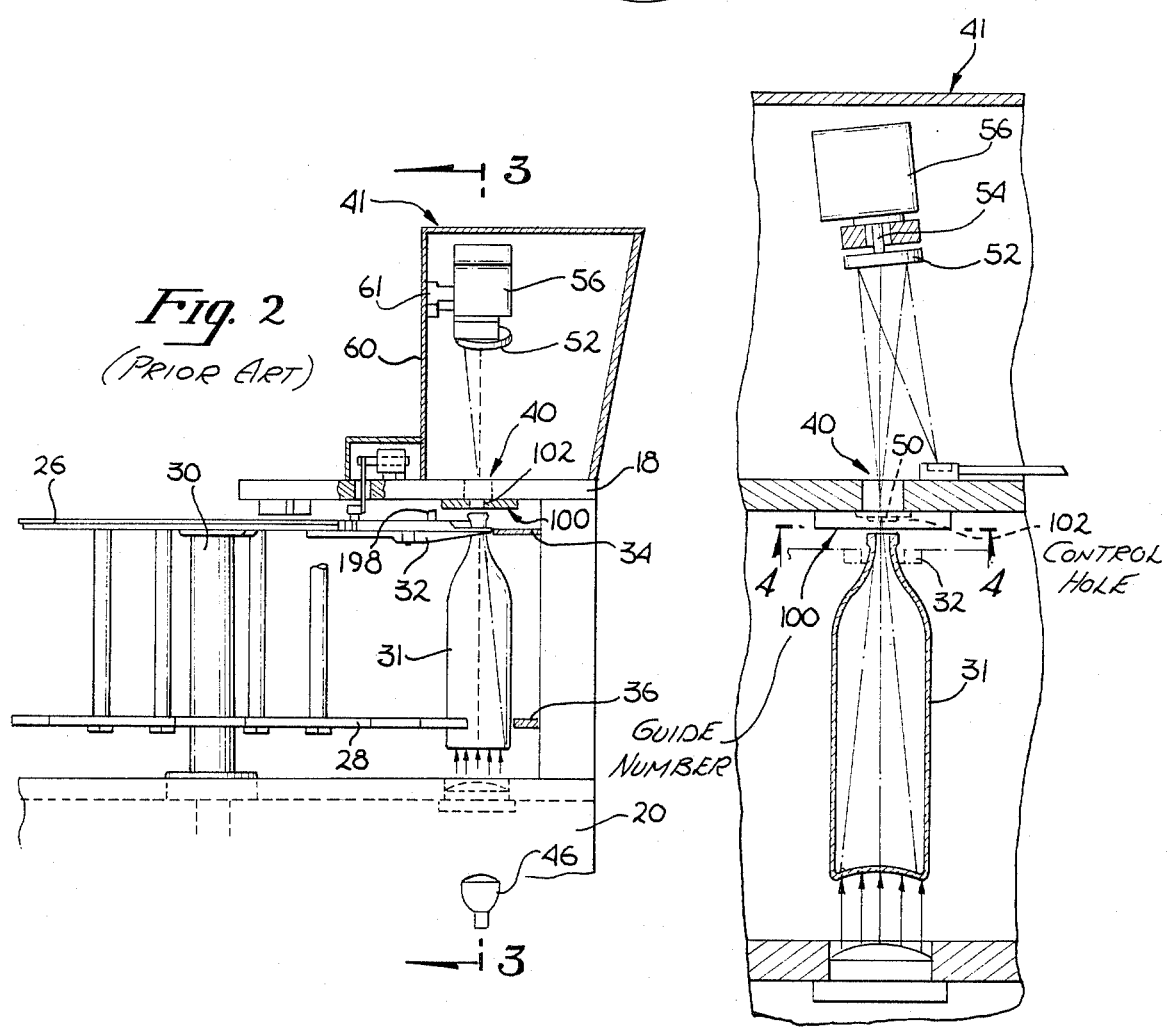
Fig. 2
(PRIOR ART)
Fig. 3
(PRIOR ART)

CHIPPED NECK INSPECTOR

This is a continuation of application Ser. No. 319,062 filed Nov. 6, 1984.

SUMMARY

A beam or pulse of energy is directed by a first energy guide to impact upon a portion of a lip of a container. The amount of energy, reflected off the lip and through a second energy guide, is measured by a sensor located at the end of the second guide. The sensor produces an output signal having a magnitude proportional to the amount of reflected energy received by the sensor. Appropriate electrical circuitry compares the magnitude of the sensor output to a preselected magnitude. If the sensor output is greater it generates a first signal indicating a first condition of that portion of the lip of the container and, if the sensor output is less it generates a second signal indicating a second condition of that portion of the lip. A plurality of such reflected beams and sensors and electrical circuits may be employed around the perimeter of the lip to determine the condition of substantially the entire lip. Alternate embodiments using alternate signal conditioning are disclosed.

DESCRIPTION OF THE FIGURES

FIG. 1 is a top plan view of a well known container inspector and sorting machine.

FIG. 2 is a cross sectional view taken along the line 2—2 of FIG. 1.

FIG. 3 is an elevational view of a typical optical path taken along line 3—3 of FIG. 2.

DETAILED DESCRIPTION OF THE INVENTION

Figure 4:
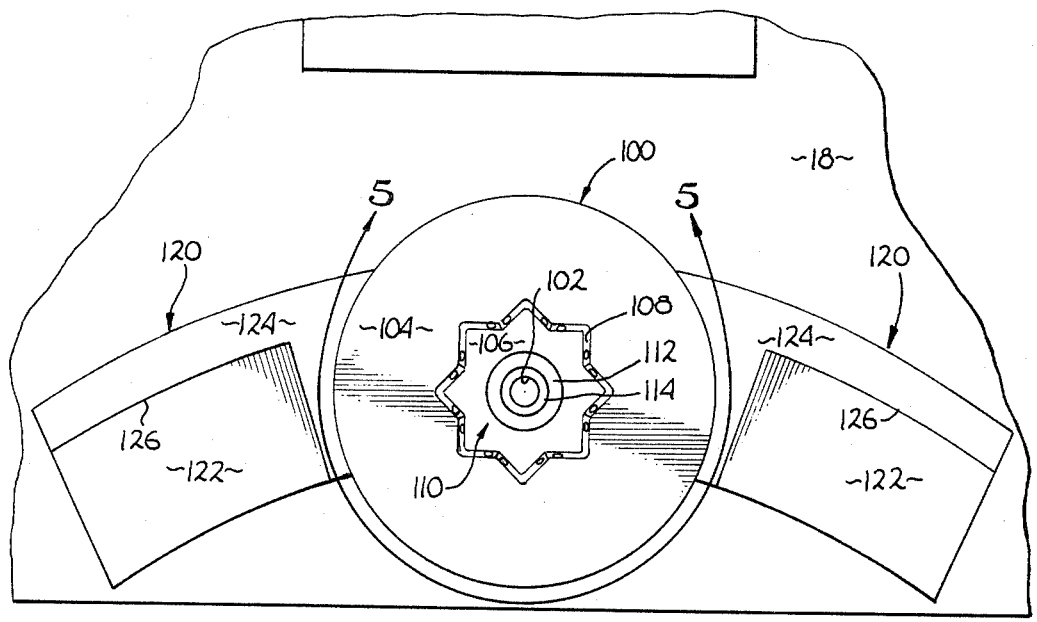
FIG. 4 is a sectional taken along the line 4—4 of FIG. 3 and shows one surface of the guide member.
Figure 5:
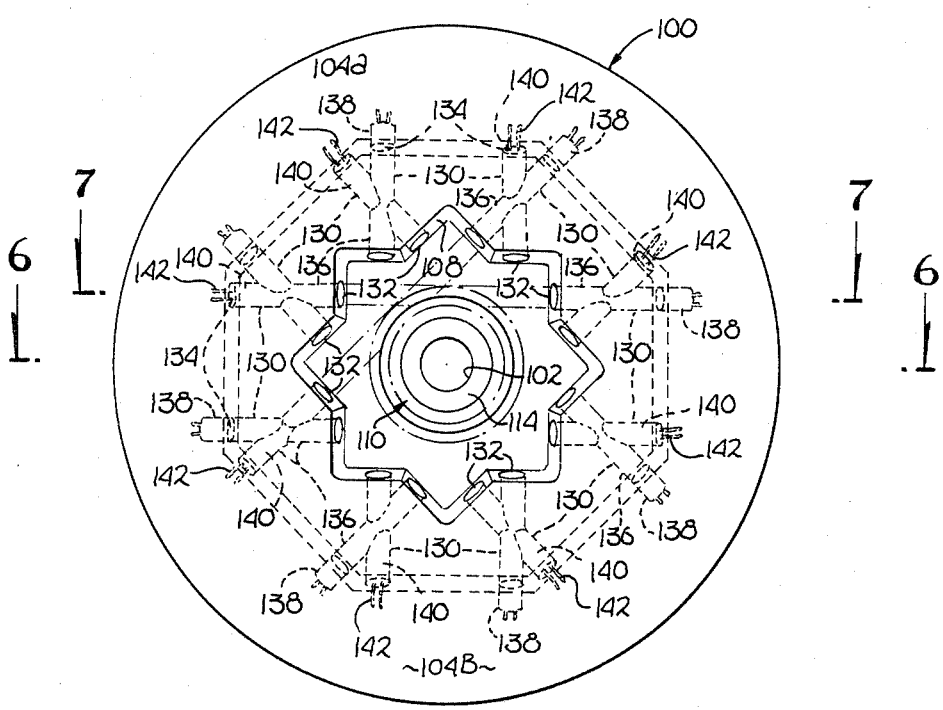
FIG. 5 is a detail view of the guide member showing the guide paths in phantom.

FIGS. 1 and 2 show a well known electronic bottle inspection machine which may be readily adapted to incorporate the present invention. A supply conveyor 24 supplies bottles to the inspection machine, which bottles are picked up by a rotating starwheel assembly comprising an upper starwheel 26 and a lower starwheel 28 supported on a central shaft 30 supported by the base 20. The individual bottles 31 are gripped by the neck thereof by grippers 32 (see also FIG. 3) to support the bottles 31 from the side, the bottles being further confined by guides 34 and 36. Also a pair of idler starwheels 38 are provided adjacent the transition between the supply conveyor 24 and the starwheels 26 and 28 to further guide the bottles in that region. The bottles pass under the inspection station or position 40 at which time they are inspected by the inspection head 41, and proceed to the delivery guides 42 to be redeposited on the conveyor 24 if they pass inspection, or to be sooner delivered to rejected bottle accumulator table 44 if the bottles do not pass inspection (A take away conveyor may also be used if desired). These aspects of the well known inspection machine are generally in accordance with the disclosure of U.S. Pat. No. 3,975,260 assigned to the assignee of the present invention.

Referring more specifically to FIGS. 2 and 3, various details of the inspection system for inspecting bottles using visible light to detect opaque foreign matter therein may be seen. FIG. 2 is a view taken in partial cross-section through the inspection position 40 and the axis of rotation of the main starwheels, as shown by the section line 2—2 in FIG. 1. FIG. 3 is a view also taken through the inspection position, though perpendicular to the section of FIG. 2, as illustrated by the section lines 3—3 of FIG. 2. An incandescent light source 46 is disposed immediately below the inspection position 40, projecting relatively diffuse light toward the bottom of the bottle 31 at the inspection position. The light passing through the bottom of the bottle and out through the neck thereof is focused by a lens 50 onto the face of a rotating scanner head 52 supported on shaft 54 of motor 56 and rotated at high speed. The motor 56 is fastened to the back wall 60 of the inspection head 41 by bracket 61 and screws (not shown). The details of operation by which such a scanner device may be utilized to inspect a bottle 31 are set forth in U.S. Pat. No. 4,221,961 assigned to the assignee of the present invention. The details of operation will not be discussed herein, and the above short description of the bottle inspection device and the scanner are set forth herein merely to introduce the reader to the inspection device and to serve as background to illustrate how easily the present invention may be added onto such bottle inspecting machines.

Figure 9:
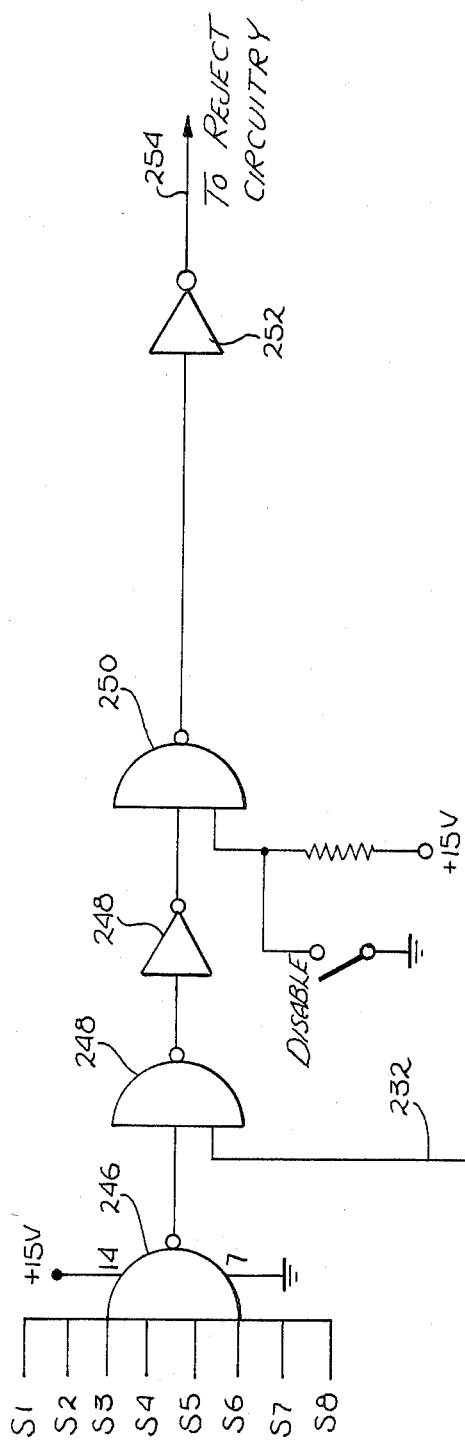
FIGS. 9 and 10 are schematic diagrams of the electronic circuitry used to generate measure and interpret the energy reflected off a container lip.
Figure 9:
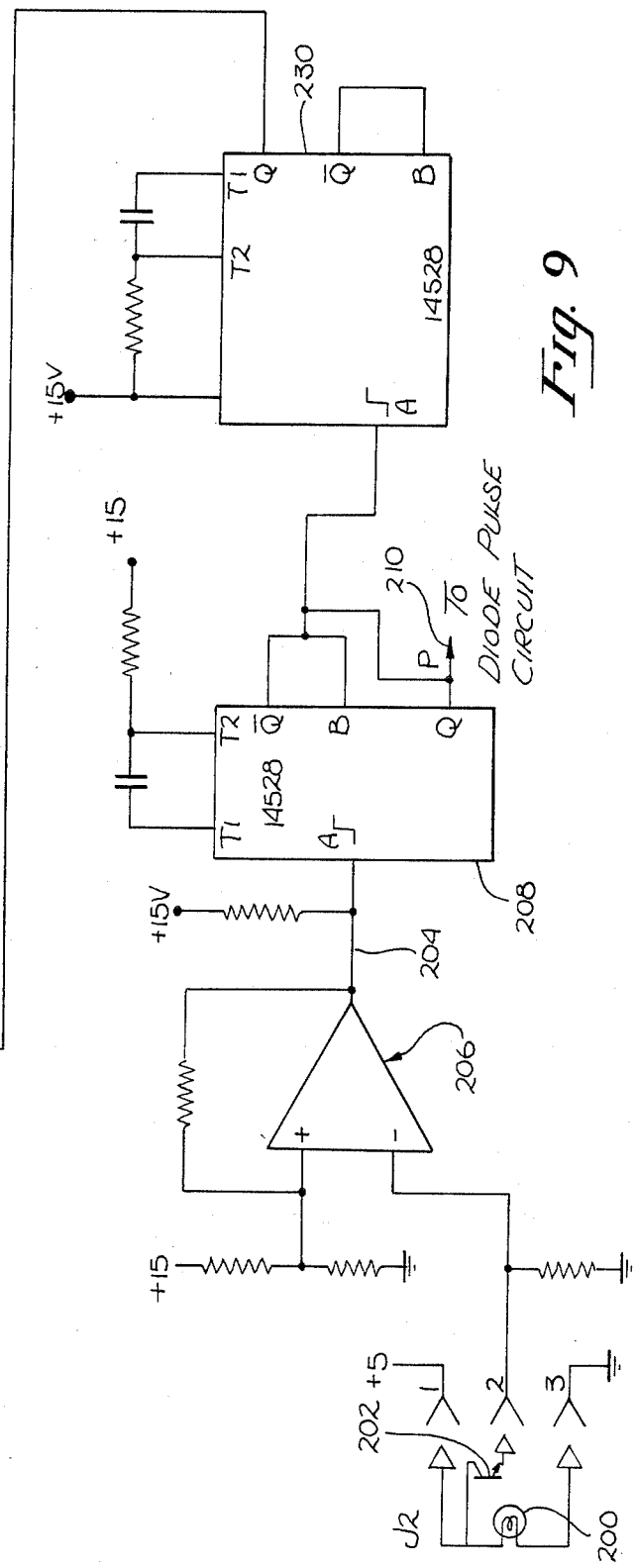
Figure 10:
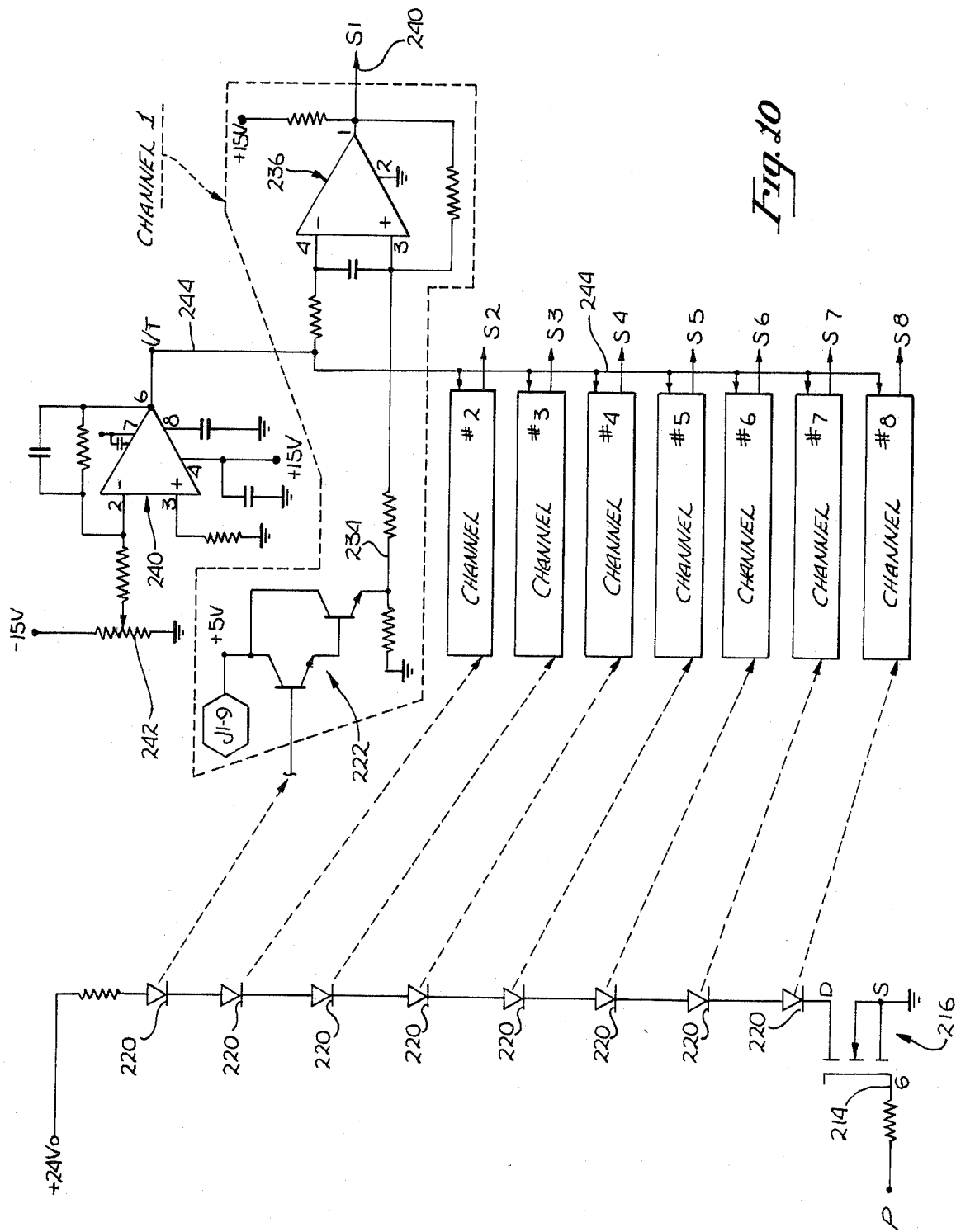

The hardware of the present invention includes the disk like guide member 100 shown immediatly above the bottle 31 and located at inspection station 40. The guide member 100 has a centrally located hole 102 therethrough vertically aligned with inspection station 40 so as not to interfere with the light originating from source 46 and traveling to scanner head 52. The physical details of guide member 100 are shown in FIGS. 4-8. The electronics of the present invention is shown in the schematics of FIGS. 9 and 10.

The guide member 100 is a generally disk like member and is shown in FIG. 4 as viewed from its underside (as seen in FIG. 3). Guide member 100 has a generally annular lowermost surface 104. The star like surface 106 is recessed with respect to surface 104 and is joined to surface 104 by star shaped sloping wall 108. A conical protrusion 110, centrally located on surface 106, is defined by conical wall 112 and the flat annular surface 114 forming the lip of conical protrusion 110. Surface 114 is located in substantially the same plane as surface 104. Located on each side of guide member 100 is a ramp member 120. Each ramp member 120 has a sloped portion 122 which is recessed from flat portion 124 by step 126 with the greatest recess being at the end of ramp 120 farthest from guide member 100. The sloped portion 122 meets the flat portion 124 adjacent the guide member 100, with flat portion 124 being slightly higher than surface 104. The conical protrusion 110 and the sloped portions 122 are provided for the same reason, i.e., to prevent an improperly positioned bottle from extending into the recess and encountering an abrupt vertical obstacle such as the circumference of guide member 100 or the sloping wall 108 and becoming jammed or wedged against that surface and possibly breaking the bottle as a result. The guide member 100 and the ramps 120 are preferably made of a suitable plastic material, such as polycarbonate, though other suitable materials may readily be used.

When viewed from its underside 104, guide member 100 shows little evidence of the many energy guide means such as guide paths 130 provided therein. The guide paths 130 are all physically identical in that each is simply a hole in the guide member 100. Each hole has two open ends, a radially inner open end 132 and a radially outer open end 134. However, half of the holes, i.e. holes 136 guide energy from an energy source 138 onto the surface of the lip of a bottle 31 being inspected, and the other half of the holes, i.e. holes 140 guide the reflected energy toward an energy sensor 142. These holes 130 (also referred to as guide means or guide paths) are not radially oriented, but are positioned so that a beam of energy directed along the longitudinal axis of the hole, will impact the lip of a container 31 at approximately the center of the annular lip of the container 31. The arrangement of the holes is best illustrated in FIGS. 5-8.

The energy sources 138 are preferably light emitting diodes. These diodes generate infrared light and can be pulsed by suitable electronic circuitry discussed below to produce a pulse of light. Other types of energy sources 138 could also be used such as visible sources, ultraviolet sources, sonic, etc. Each type would have its own unique characteristics, but in theory could be adapted for the intended use. Of course the nature of the sensor 142 would have to correspond to the type of energy source. The light emitting diodes are preferred however, as they are simple and inexpensive, may be pulsed at relatively high energy levels to provide a short high energy, readily controlled "flash", and emit light in wavelengths that have the desired reflection characteristics with glass and are easily sensed to provide a high signal to noise ratio with respect to noise from ambient light conditions.

Figure 6:
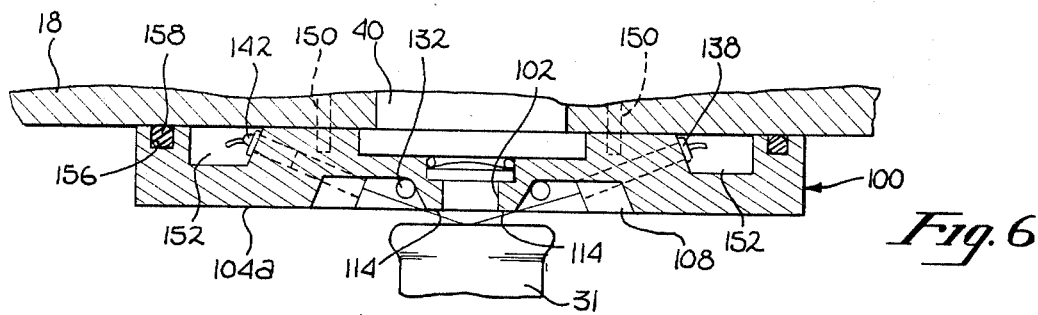
FIG. 6 is a cross sectional view taken through the center of the guide member along the line 6—6 of FIG. 5.

A cross-section through a diameter of the guide member 100 as shown in FIG. 6 reveals the ease with which the guide member 100 may be secured to existing electronic bottle inspection machines. The guide member 100 is secured to the existing machinery co-axially with inspection station 40 by four screws 150 two of which are shown. All the electrical wiring to make connections with the energy sources 138 and the energy sensors 142 is located in the generally annular volume designated 152 located about the perimeter of the radially outer ends 134 of the holes 130. The wiring is bundled together and directed upward through a hole in plate 18. A second annular cavity 156 is located near the perimeter of guide member 100 for receiving an O-ring 158 which maintains a sealed relationship between plate 18 and guide member 100 when screws 150 are sufficiently tightened.

Figure 7:
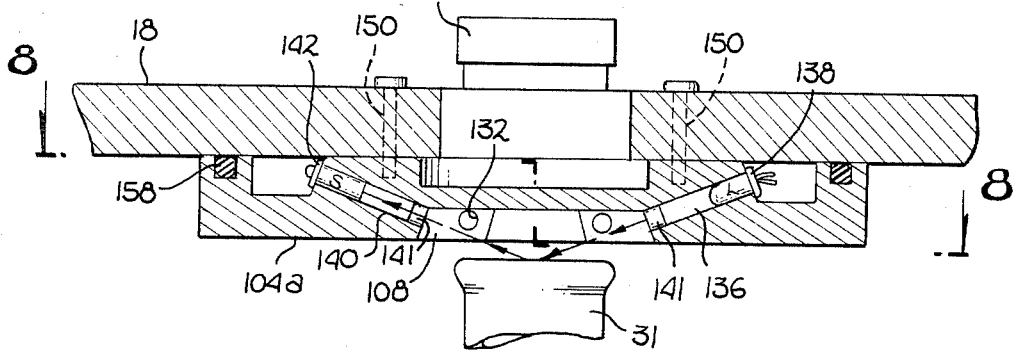
FIG. 7 is a cross-sectional view taken along the line 7—7 through the guide member.
Figure 8:
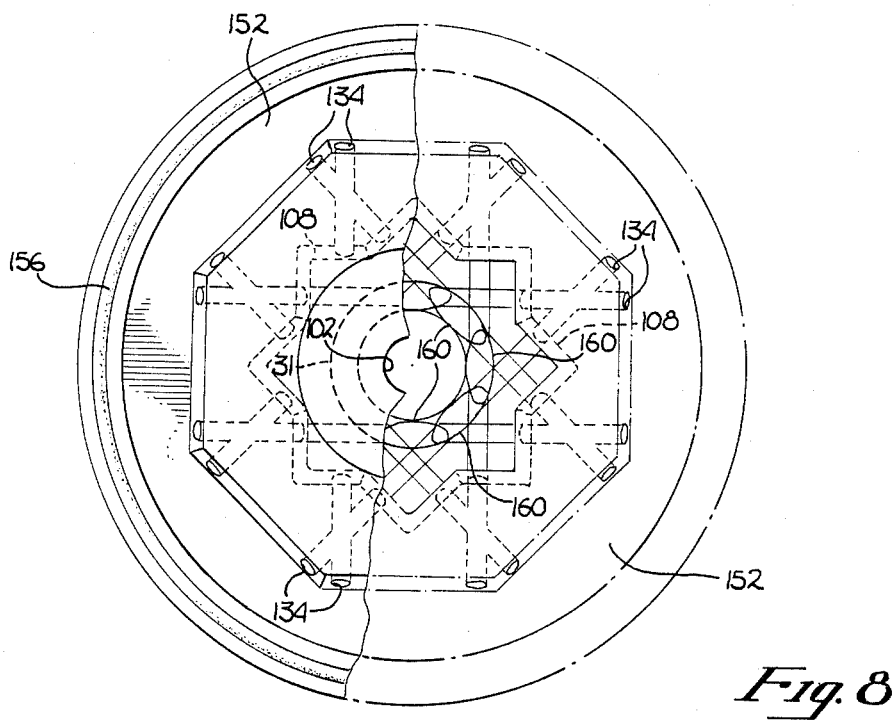
FIG. 8 is a partial cutaway view taken along the line 8—8 of FIG. 7 showing the coverage pattern of the multiple beams of energy.

The function of the guide member 100 is best illustrated in FIGS. 7 and 8. FIG. 7 shows a single energy source 138 mounted on the radially outer end of a hole 136 and a corresponding energy sensor 142 mounted on the radially outer end of hole 140. These holes 136 and 140 are both positioned at the same angular displacement (20 degrees in the preferred embodiment although a range of approximately 10 degrees to 30 degrees or more can be used) with respect to the plane of the lip of the bottle 31. When a bottle 31 is positioned directly beneath the inspection station 40, the electronic circuitry (described below) activates (pulses) the energy source 138. The energy is guided down hole 136 and intercepts the lip of the bottle. If the lip is in good condition, the energy will be reflected into and guided by hole 140 where it will be detected by energy sensor 142. If the lip of the bottle is chipped or fractured, the energy (e.g. light) will be scattered and only a very small amount, if any, will be reflected at the angle necessary to be detected by sensor 142. Since the output signal of the sensor 142 is responsive to the amount of energy detected, the output of a sensor 142 may be used as an indication of the condition of the lip (i.e., good or chipped). A number of energy sources 138, and energy sensors 142 as well as holes 136 and 140 may be positioned around the guide member 100 to determine the condition of substantially the entire lip of a bottle as shown in FIG. 8. In the preferred embodiment, the ends of the holes within which the sources and sensors reside are covered with a transparent plug 141 so that foreign matter cannot accumulate in the holes to affect performance of the system.

Eight energy sources 138 and eight energy sensors 142 are used in the configuration of FIG. 8 to provide eight slightly overlapping eliptical test regions 160 which collectively test substantially the entire lip of the bottle 31. If any of the sensors 142 produce an output signal below a preselected threshold level, the electronics will activate the reject mechanism of the bottle inspection machine to direct the bottle to follow a path leading to an accumulator table 44 for rejected bottles.

The electronic circuitry used to activate the energy sources 138, to set the threshold level for the energy sensors 142, to determine whether each sensor output is above that threshold, and if not to activate the reject mechanism, is shown in FIGS. 9 and 10.

The lip inspection sequence (and bottle inspection) begins when a trigger pin 198 located on starwheel 26 breaks a light beam originating with light source 200 and shining on the trigger phototransistor 202. The trigger pin 198 is positioned to break the light beam when a bottle 31 reaches inspection position 40. When the beam is broken phototransistor 202 stops conducting, which causes the output signal on line 204 of voltage comparator 206 to change from a logical low state to a logical high state (Alternatively, a shaft encoder on the starwheel may also be used). The signal on line 204 is an input signal to a 74121 one shot 208, a current pulse one-shot. When the signal on line 204 changes to the high state, it triggers the one-shot 208. The one-shot 208 generates a current pulse at output terminal Q, appearing as signal P on line 210. Signal P (see FIG. 10) drives the gate of a VMOS field effect transistor (FET) 212 configured as a voltage amplifier. The output of VMOS FET 212 drives the gate 214 of another VMOS FET 216 acting as an off/on switch. When the VMOS FET 216 is in the on state, current flows through the energy sources 138 which in FIG. 10 comprise the eight light emitting diodes 220. The duration of current flow through diodes 220 is determined by one-shot 208. As configured in FIG. 9 this duration is approximately 20 microseconds. The duration is chosen to encompass the response time of the LEDs 220 and the response time of the energy sensors 142 which comprise photo-darlington transistor pairs 222 in FIG. 10. By keeping the pulse time relatively short, the duty cycle of the LED's is very low, thereby allowing a relatively high energy pulse to be used in comparison to the steady state capability of the LEDs. This, combined with the directional characteristics resulting from the position of the sources and sensors in the respective holes, assures a good signal level and lack of influence of background lighting.

On the trailing edge of the current pulse output by one-shot 208, another one-shot 230 (see FIG. 9) is triggered for approximately 1 microsecond. This 1 microsecond pulse will be referred to as the "look-interval" window, and appears at the Q output of one shot 230 on line 232.

In the preferred embodiment of the invention, the lip of a container is conceptually divided into eight regions. Thus eight energy sources 138 and eight energy sensors 142 must be employed. If eight light emitting diodes 220 are used, eight photo-darlington transistor pairs 222 are also used. The output of each photo-darlington transistor pair 222 is applied over line 234 to one input terminal of a respective comparator 236. A threshold voltage is applied to the other input terminal of the comparator 236. The comparator 236 generates an output signal on line 240 which is at a first logical level if the darlington output is greater than the threshold and is at a second logical level if the darlington output is less than the threshold. A darlington pair 222 and its associated comparator 236 may be referred to as a channel of electronics. The output signals $S_1$ through $S_8$ of each channel (i.e. the output of a respective comparator 236) assume a first state or a second state depending on whether the darlington output is above or below a preselected threshold level. The circuitry within each of the eight channels is identical.

The threshold voltage $V_T$ for all eight channels is generated by the single op-amp 240. A variable resistor 242 determines what portion of a $-15$ volt source is applied to an input terminal of the op-amp 240, thereby setting the threshold voltage $V_T$. The threshold voltage $V_T$ is empirically selected and provided over line 244 to each channel (1 through 8) of the electronics.

The output signal of each channel, i.e. signals $S_1$ through $S_8$ are Anded at AND gate 246. The output of AND gate 246 is Anded with the "look interval" signal by AND gate 248. If any one or more of signals $S_1$ through $S_8$ is not present (true) at the input of AND gate 246 (indicating that the sensor 142 for that channel received less energy than it should have to indicate a "good condition" of the area of the lip which it inspects) AND gate 246 will output a logical true signal to so indicate. If the true signal from AND gate 246 (indicating a reject condition) is present during the "look interval" represented by the one microsecond pulse on line 232, AND gate 248 will output a logical false signal which will be propagated through AND gate 250 and op-amp 252 to generate a signal on line 254 to activate the reject mechanism (well known in the art) to cause the rejected bottle to be directed to the storage corral 44. If all sensors 142 generate output signals above the set threshold $V_T$, the output of AND gate 246 will be logical false and no reject signal will be generated. The inspected bottle, if not rejected by other tests, will then be allowed to follow the path to the station where the bottle filing (or other) operation is performed.

The electronics of FIGS. 9 and 10 are readily and advantageously located within inspection head 41 and communicate over lines 260, with the energy sources 138 and energy sensors 142, through hole 154 in guide member 100.

The above described container lip inspection system has a number of advantages over techniques employed in the prior art to inspect and/or detect defects on the lip of containers, particularly the sealing surface of glass bottles used for carbonated beverages. In particular, one prior art technique was to inspect the bottles visually as they passed on a conveyor. This technique however, aside from being expensive because of the manpower requirements, is less than ideal because of the inaccuracy in the inspection caused by the rate at which bottles normally pass by a person for inspection. In that regard, it is common in bottling plants to not require any one individual to inspect bottle necks for sustained periods of time because of the rigorous demands of such inspection. Also, bottles having chipped or broken necks would sometimes be detected at the filling machine, though generally with adverse affects when detected at such a late stage of the bottling procedure in particular. Carbonated beverages are bottled by first bringing a filling head firmly against the bottle top so that a rubber gasket therebetween will seal on a good bottle, after which the bottle is pressurized and then filled with a carbonated beverage. If the bottle lip is badly chipped, an inadequate seal will be achieved between the filling head and the bottle so that the bottle will not properly pressurize, in which case the filling head will not proceed with the filling thereof. The question always remains of course, as to where the chip or chips went as they could cling to or pierce the sealing gasket so as to cling thereto until the next bottle to be filled by the same head, possibly falling into the next bottle during the filling operation. In the case of small chips the bottle will normally fill, but the cap will not seal so that the beverage will go flat (and possibly have a glass chip in it) well before it reaches the consumer. Finally, badly cracked bottles will sometimes crush under the pressure of the filling head, in which case the filling machine is almost always stopped for careful cleaning of the filling gasket to remove any shards of glass that might have become embedded in the gasket. Consequently, the present invention is highly advantageous to eliminate faulty bottles prior to the filling machine, thereby resulting in fewer shutdowns of the filling machines for cleaning of the filling heads, for reducing the number of bottles which will not properly seal in the capping operation, and probably for reducing the likelihood that glass chips and the like will inadvertently be bottled along with each soft drink.

Figure 11:
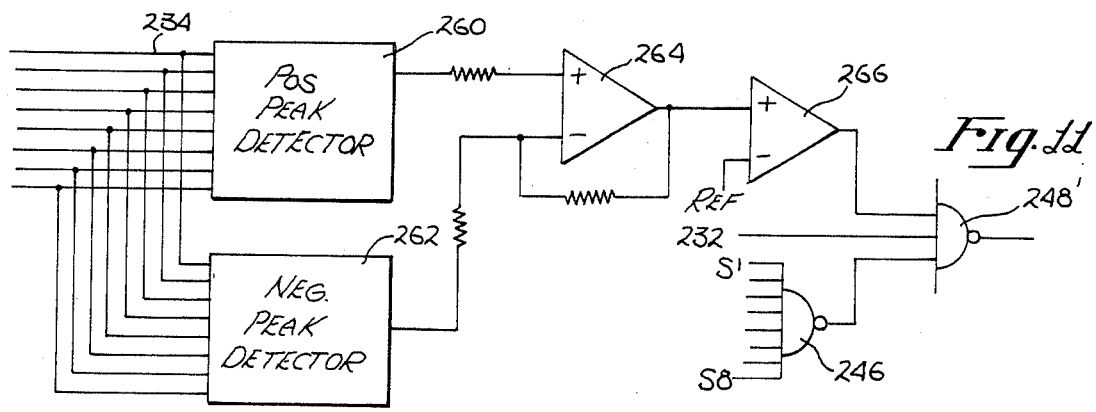

With the present invention, containers of different color and texture, and undoubtedly containers made of materials other than glass, can be inspected by the present invention by appropriate adjustment of the threshhold voltage in accordance with the reflective characteristics of the material. In that regard, the basic sensing system of the present invention is not necessarily limited to use with the preferred electronics disclosed herewith, but other signal processing and conditioning systems may readily be used as desired. By way of one specific example, the present invention has been used in conjunction with electronics responsive to two conditions rather than the single condition herein described. In particular, in the preferred embodiment disclosed herein, the determination that the sealing surface on a bottle is not chipped is made by noting that none of the signals on the eight channels has fallen below the preset reference voltage. In the other form of electronics, a second condition was also imposed, specifically that the highest channel signal and the lowest channel signal should not differ by some second reference amount. This may be achieved by the circuit of FIG. 11 wherein the positive and negative peaks the signals on lines 234

(FIG. 10) of each channel are detected by diode peak detectors 260 and 262, the difference taken by amplifier 264 and threshold detected by comparator 266 to provide an additional input signal for NAND gate 248', the output of which is identical in form and function to be the output of NAND gate 248 of FIG. 9. This second condition was originally contemplated as being appropriate for allowing for some dulling or frosting of the sealing surface of older returnable bottles, a uniform dulling tending to indicate such frosting and a non uniform dulling suggesting the presence of a chip in an otherwise somewhat frosted sealing surface. It was found however, that the single inspection condition of the preferred embodiment disclosed herein provided an adequate test and that the inclusion of the second condition that the bottle lip be substantially uniform over its entire periphery added a complexity to the system without enhancement of its operating characteristics. It is to be understood however, that different and/or additional conditions of acceptance and rejection may readily be incorporated and the electronics changed accordingly without departing from the present invention.

Figure 12:
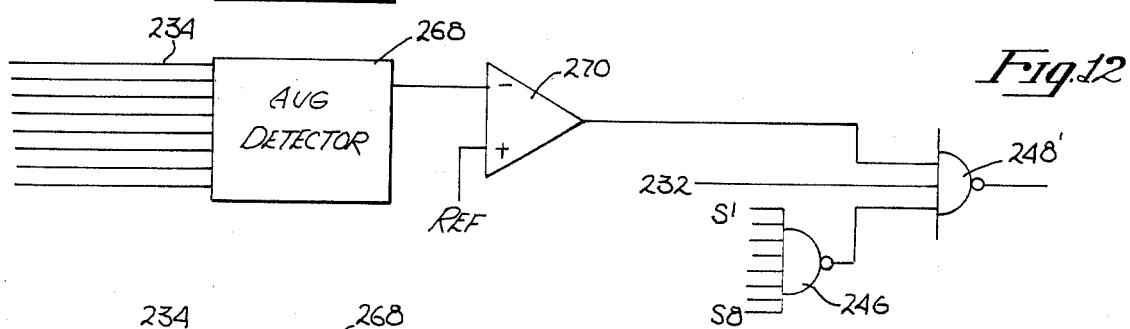
Figure 13:
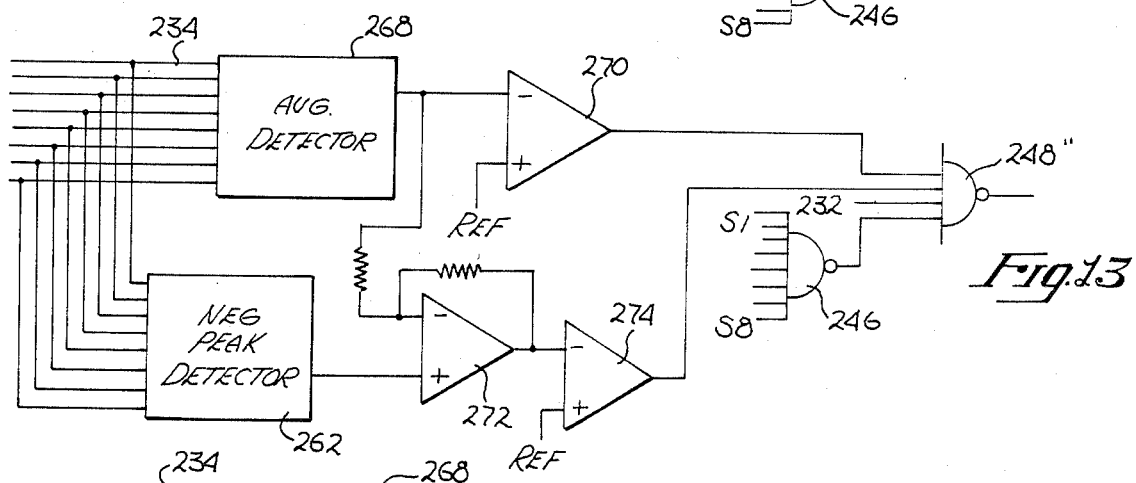
Figure 14:
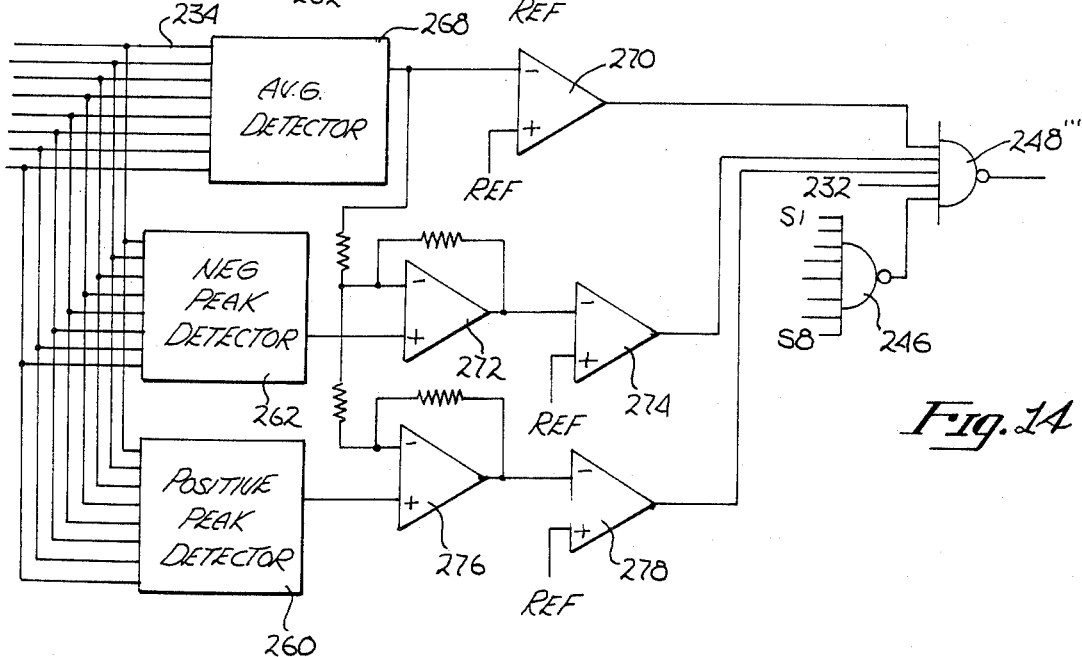

As an example of a different and/or additional condition of acceptance and rejection, the output signals of the sensors may be averaged to provide an average signal indicative of the general reflective characteristics of the top of the bottle. A circuit operative on the average signal is shown in FIG. 12, wherein the signals on lines 234 (FIG. 10) of each channel are averaged by averaging circuit 268, effectively inverted and threshold detected by comparator 270, and then applied to NAND gate 248' as before. A new bottle may have a relatively high average value, whereas an older bottle may have the top surface somewhat frosted, resulting in a lower average value. Other factors, of course, may also affect the average value so that different average values may be expected even for new bottles. Generally, using this technique, a first limit is placed on the average value, specifically a lower limit on the average value, as certain conditions on the top of the bottle giving cause for rejection thereof are characterized by a low average value. These conditions include a very large chip or break at the top of the bottle wherein a large part or all of the sealing surface is missing. A second limitation is also imposed on the difference between the average signal and the lowest sensor signal, so that a local chip which lowers one sensor signal substantially but does not pull the average down sufficiently to cause a reject based on that average will be sensed by the unacceptable difference between that low signal and the average signal. This may be accomplished by a modification of the circuit of FIG. 12, as shown in FIG. 13, specifically by the addition of a negative peak detector 262, a differential amplifier coupled to take the difference between the average and the negative peak, and a comparator 274 to threshold detect the difference with proper polarity, to provide a still further signal to NAND gate 248'. Finally, certain types of chips will leave a smooth glossy surface which, if oriented properly, may result in a higher reflection, and thus a higher sensed signal, than unchipped areas of the same bottle top. To sense flaws of this character, a third limitation is imposed, this limitation being that the highest sensor signal cannot exceed the average by more than a predetermined amount. This may be achieved by a modification of the circuit of FIG. 13, as shown in FIG. 14, to add to positive peak detector 260, a differential amplifier to take the difference between the positive peak and the average, and a comparator 278 to provide a still further input to NAND gate 248'. In this embodiment as well as in other embodiments, it is preferable to make the inspection limits manually adjustable, as frequently good bottles, even new bottles will exhibit certain variation around the top thereof, depending upon the quality of the molding of the bottles, which variations should not become a basis of rejection, and manual adjustment will allow optimization of the inspection function for the range of bottles being inspected.

In the preferred embodiment, the holes containing the light sources and light sensors are inclined with respect to the plane of the top of the bottles to be inspected by approximately 20 degrees. With this angle, the eight areas 160 (see FIG. 8) which are covered by the light sources and viewed by the light sensors will slightly overlap so as to cover the entire lip of the container. Further, while larger or smaller angles may be used, it is generally preferred that the angle remain in the range of 10 to 30 degrees as particularly shallow angles, i.e., less than 10 degrees, result in a system which is too sensitive to bottle height (which is not a carefully controlled parameter in most bottle types) and too steep an angle, i.e., over 30 degrees, tends to illuminate too small a portion of the bottle lip so that unnecessarily large numbers of light sources and sensors are required to cover the entire sealing surface. Also the fraction of light reflected for detection diminishes rapidly at larger angles. Further, with respect to the orientation of the illumination of the top of the bottle, it should be noted that the embodiment disclosed herein in detail as exemplary of the preferred embodiment illuminates the top of the bottle in a relatively circumferential manner. This is by no means a limitation on the invention however, as the light sources and light sensors may be disposed on diametral lines so that the illumination and viewing of the top of the bottle is fundamentally radial as opposed to circumferential. Obviously any angle therebetween is also suitable.

Also in the preferred embodiment disclosed herein, the chipped neck inspector is positioned coaxially with a prior art empty bottle inspector so that the neck inspection is achieved at the same time as the bottom of the bottle is inspected. Thus, not only are the two inspections accomplished at the same inspection position of the bottle, but the chipped neck inspector may be triggered by the same trigger pin and sensor combination as is used to trigger the empty bottle inspector itself. This of course also is by no means a limitation on the present invention, as the chipped neck inspector may be positioned noncoaxially with the empty bottle inspection system with its own trigger system. For that matter the chipped neck inspector might well be used in a stand alone system wherein the chipped neck inspector is triggered and the neck inspection is accomplished in apparatus separate and apart from any other inspection function or apparatus.

While the invention has been described with particular reference to the preferred embodiment and FIGS. 1 through 10, it should be understood that many modifications of structure, material and other characteristics can be made by one of ordinary skill in the art without departing from the spirit and scope of the invention. The Figures and description are included by way of illustration and not as limitations upon that scope. Cicuits other than those discussed herein can readily be devised to perform the same functions, and energy sources presently available as well as those that may become available in the future, might readily by suitable or adaptable for use in the present invention. The invention is not intended to be limited by the specific nature of the energy employed nor the shape of the guide member used to define the path of the energy. The spirit and scope of the invention is only intended to be limited by the scope of the appended claims.

What is claimed is:

1. A system for detecting the condition of the lip of a container comprising:

at least one stationary source of pulsed energy;

guide means for guiding said energy from said at least one source of pulsed energy to form a plurality of beams of energy directed toward and distributed around the lip of said container, each of said beams directing energy toward an area of the lip of such container substantially unique to that beam;

a plurality of stationary sensor means equal in number to said plurality of beams of energy, each for generating an electrical signal responsive to the amount of energy reflected by said lip and incident to said respective sensor means, said guide means further being a means to substantially limit the energy incident to each said sensor means to that originating from an associated one of said plurality of beams of energy and reflected by the respective area of the lip of said container unique thereto; and output means coupled to said plurality of sensor means and simultaneously responsive to said electrical signals therefrom to provide an output signal indicative of the condition of the lip of said container.

2. The system according to claim 1 wherein said guide means directs the energy from said at least one source of pulsed energy to collectively intercept substantially the entire surface of the lip of said container.

3. The system of claim 1 further including trigger means for pulsing said at least one source of pulsed energy and for enabling said output means when a container is aligned with said guide means.

4. The system of claim 3 further comprised of means for sequentially moving containers to be inspected past said guide means.

5. The system of claim 4 further comprised of electronic bottle inspection means substantially coaxial with said guide means for substantially simultaneously inspection of the bottle bottom and lip.

6. The system according to claim 1 wherein said energy is directed at an angle between approximately 10 and 30 degrees to the plane of the lip, and in a plane tangential to the circumference of the lip.

7. The system according to claim 6 wherein said angle is substantially 20 degrees.

8. The system according to claim 1 wherein said output means is responsive to the output of the sensor means having the lowest level of light incident thereon to provide said output signal indicative of the condition of the lip of said container.

9. The system according to claim 8 wherein said output means is also responsive to the difference in output between the sensor means having the lowest level of light incident thereto and the sensor means having the highest level of light incident thereto to provide said output signal indicative of the condition of the lip of said container.

10. The system according to claim 1 wherein said output means is responsive to the average of the outputs of said sensors means to provide said output signal indicative of the condition of the lip of said container.

11. The system according to claim 10 wherein said output means is also responsive to the difference between said average of the outputs of said sensor means and the output of the sensor means having the lowest level of light incident thereon to provide said output signal indicative of the condition of the lip of said container.

12. The system according to claim 11 wherein said output means is also responsive to the difference between said average of the outputs of said sensors means and the output of the sensor means having the highest level of light incident thereon to provide said output signal indicative of the condition of the lip of said container.

* * * * *